(12) United States Patent
Shepherd et al.

(10) Patent No.: US 11,689,378 B1
(45) Date of Patent: Jun. 27, 2023

(54) DETERMINING LOSS OF FOCUS IN ONLINE SESSIONS

(71) Applicant: Dell Products L.P., Round Rock, TX (US)

(72) Inventors: Michael Shepherd, Leander, TX (US); Jonathan Whitson, Oklahoma City, OK (US)

(73) Assignee: DELL PRODUCTS L.P., Round Rock, TX (US)

( * ) Notice: Subject to any disclaimer, the term of this patent is extended or adjusted under 35 U.S.C. 154(b) by 0 days.

(21) Appl. No.: 17/581,263

(22) Filed: Jan. 21, 2022

(51) Int. Cl.
  *H04L 12/18* (2006.01)
  *G16H 40/67* (2018.01)
(52) U.S. Cl.
  CPC ......... *H04L 12/1813* (2013.01); *G16H 40/67* (2018.01)
(58) Field of Classification Search
  CPC .......................... H04L 12/1813; G16H 40/67
  USPC ...................................................... 340/573.1
  See application file for complete search history.

(56) References Cited

U.S. PATENT DOCUMENTS

| | | | | |
|---|---|---|---|---|
| 2013/0258042 | A1* | 10/2013 | Shun | H04N 7/152 348/E7.083 |
| 2017/0177928 | A1* | 6/2017 | Cunico | H04L 65/403 |
| 2019/0109660 | A1 | 4/2019 | Akins, III | |
| 2020/0076566 | A1 | 3/2020 | Andrade Alfonseca et al. | |

FOREIGN PATENT DOCUMENTS

CN          112085630 A  * 12/2020 ......... G06F 16/9535

OTHER PUBLICATIONS

Shepherd, et al. "Bio-Telemetry Extraction from Online Sessions" U.S. Appl. No. 17/581,594, filed Jan. 21, 2022, 39 pages.
Shepherd, et al. "Information Extraction from Live Online Sessions" U.S. Appl. No. 17/678,758, filed Feb. 23, 2022, 40 pages.
Office Action dated Mar. 17, 2023 for U.S. Appl. No. 17/581,594, 11 pages.

* cited by examiner

*Primary Examiner* — Omar Casillashernandez
(74) *Attorney, Agent, or Firm* — Amin, Turocy & Watson, LLP

(57) ABSTRACT

A system can receive respective bio telemetry data from a group of people in an online session, wherein the bio telemetry data comprises alpha wave data and beta wave data. The system can determine a current moving average for the current time period based on a numerical combination of respective beta wave data of the bio telemetry data and respective alpha wave data of the bio telemetry data, wherein the numerical combination is scaled by a first weighting value, wherein the current moving average is decreased by a previous moving average for a previous time period, and wherein the previous moving average is scaled by a second weighting value. The system can, in response to determining that attentiveness by the group of people has decreased based on the previous moving average being greater than the current moving average, sending attentiveness notification data directed to an instructor user account.

20 Claims, 8 Drawing Sheets

400

RECEIVING RESPECTIVE BIO TELEMETRY DATA FROM A GROUP OF PEOPLE IN AN ONLINE SESSION, WHEREIN THE BIO TELEMETRY DATA COMPRISES ALPHA WAVE DATA AND BETA WAVE DATA, WHEREIN THE BIO TELEMETRY DATA SPANS A CURRENT TIME PERIOD 404

DETERMINING A CURRENT MOVING AVERAGE FOR THE CURRENT TIME PERIOD BASED ON A NUMERICAL COMBINATION OF RESPECTIVE BETA WAVE DATA OF THE BIO TELEMETRY DATA AND RESPECTIVE ALPHA WAVE DATA OF THE BIO TELEMETRY DATA, WHEREIN THE NUMERICAL COMBINATION IS SCALED BY A FIRST WEIGHTING VALUE, WHEREIN THE CURRENT MOVING AVERAGE IS DECREASED BY A PREVIOUS MOVING AVERAGE FOR A PREVIOUS TIME PERIOD, AND WHEREIN THE PREVIOUS MOVING AVERAGE IS SCALED BY A SECOND WEIGHTING VALUE 406

IN RESPONSE TO DETERMINING THAT ATTENTIVENESS BY THE GROUP OF PEOPLE HAS DECREASED BASED ON THE PREVIOUS MOVING AVERAGE BEING GREATER THAN THE CURRENT MOVING AVERAGE, SENDING ATTENTIVENESS NOTIFICATION DATA DIRECTED TO A USER ACCOUNT ASSOCIATED WITH AN INSTRUCTOR OF THE ONLINE SESSION 408

RECEIVING RESPECTIVE BIO TELEMETRY DATA FROM A GROUP OF PEOPLE THAT ARE PARTICIPANTS IN AN ONLINE MEETING, WHEREIN THE BIO TELEMETRY DATA COMPRISES ALPHA WAVE DATA AND BETA WAVE DATA, AND WHEREIN THE BIO TELEMETRY DATA SPANS A CURRENT TIME PERIOD 504

DETERMINING A CURRENT MOVING AVERAGE FOR THE CURRENT TIME PERIOD BASED ON A NUMERICAL COMBINATION OF RESPECTIVE BETA WAVE DATA OF THE BIO TELEMETRY DATA AND RESPECTIVE ALPHA WAVE DATA OF THE BIO TELEMETRY DATA, WHEREIN THE NUMERICAL COMBINATION IS SCALED BY A FIRST WEIGHTING VALUE, WHEREIN THE CURRENT MOVING AVERAGE IS DECREASED BY A PREVIOUS MOVING AVERAGE FOR A PREVIOUS TIME PERIOD, AND WHEREIN THE PREVIOUS MOVING AVERAGE IS SCALED BY A SECOND WEIGHTING VALUE 506

IN RESPONSE TO DETERMINING THAT THE PREVIOUS MOVING AVERAGE IS GREATER THAN THE CURRENT MOVING AVERAGE BY AT LEAST A THRESHOLD AMOUNT, SENDING, BY THE SYSTEM, ATTENTIVENESS NOTIFICATION DATA TO A USER ACCOUNT ASSOCIATED WITH THE ONLINE MEETING 508

CREATING MULTIPLE GROUPS OF MOVING AVERAGES, WHEREIN THE MULTIPLE GROUPS OF MOVING AVERAGES COMPRISES THE CURRENT MOVING AVERAGE AND THE PREVIOUS MOVING AVERAGE, WHEREIN RESPECTIVE GROUPS OF MOVING AVERAGES OF THE MULTIPLE GROUPS OF MOVING AVERAGES COMPRISE A SAME NUMBER OF MOVING AVERAGES 704

DETERMINING THAT THE PREVIOUS MOVING AVERAGE IS GREATER THAN THE CURRENT MOVING AVERAGE BY AT LEAST THE THRESHOLD AMOUNT BASED ON DETERMINING THAT A FIRST GROUP OF MOVING AVERAGES OF THE GROUPS OF MOVING AVERAGES IS GREATER THAN A SECOND GROUP OF MOVING AVERAGES OF THE GROUPS OF MOVING AVERAGES 706

DETERMINING LOSS OF FOCUS IN ONLINE SESSIONS

BACKGROUND

Online sessions can comprise multi-participant video meetings conducted with computers that communicate across a communications network.

SUMMARY

The following presents a simplified summary of the disclosed subject matter in order to provide a basic understanding of some of the various embodiments. This summary is not an extensive overview of the various embodiments. It is intended neither to identify key or critical elements of the various embodiments nor to delineate the scope of the various embodiments. Its sole purpose is to present some concepts of the disclosure in a streamlined form as a prelude to the more detailed description that is presented later.

An example system can operate as follows. The system can receive respective bio telemetry data from a group of people in an online session, wherein the bio telemetry data comprises alpha wave data and beta wave data, wherein the bio telemetry data spans a current time period. The system can determine a current moving average for the current time period based on a numerical combination of respective beta wave data of the bio telemetry data and respective alpha wave data of the bio telemetry data, wherein the numerical combination is scaled by a first weighting value, wherein the current moving average is decreased by a previous moving average for a previous time period, and wherein the previous moving average is scaled by a second weighting value. The system can, in response to determining that attentiveness by the group of people has decreased based on the previous moving average being greater than the current moving average, sending attentiveness notification data directed to a user account associated with an instructor of the online session.

A method can comprise receiving, by a system comprising a processor, respective bio telemetry data from a group of people that are participants in an online meeting, wherein the bio telemetry data comprises alpha wave data and beta wave data, and wherein the bio telemetry data spans a current time period. The method can further comprise determining, by the system, a current moving average for the current time period based on a numerical combination of respective beta wave data of the bio telemetry data and respective alpha wave data of the bio telemetry data, wherein the numerical combination is scaled by a first weighting value, wherein the current moving average is decreased by a previous moving average for a previous time period, and wherein the previous moving average is scaled by a second weighting value. The method can further comprise, in response to determining that the previous moving average is greater than the current moving average by at least a threshold amount, sending, by the system, attentiveness notification data to a user account associated with the online meeting.

An example non-transitory computer-readable medium can comprise instructions that, in response to execution, cause a system comprising a processor to perform operations. These operations can comprise receiving bio telemetry data for a person in an virtual meeting, wherein the bio telemetry data comprises alpha wave data and beta wave data. These operations can further comprise determining a current moving average for a current time period based on the beta wave data, numerically combined with the alpha wave data, wherein the alpha wave data is scaled by a first weighting value, wherein the current moving average is decreased by a previous moving average for a previous time period, and wherein the previous moving average is scaled by a second weighting value. These operations can further comprise, in response to determining that the previous moving average is threshold greater than the current moving average, sending a notification to a user account associated with the virtual meeting.

BRIEF DESCRIPTION OF THE DRAWINGS

Numerous embodiments, objects, and advantages of the present embodiments will be apparent upon consideration of the following detailed description, taken in conjunction with the accompanying drawings, in which like reference characters refer to like parts throughout, and in which:

FIG. 4 illustrates another example process flow that can facilitate determining loss of focus in online sessions, in accordance with an embodiment of this disclosure;

FIG. 5 illustrates another example process flow that can facilitate determining loss of focus in online sessions, in accordance with an embodiment of this disclosure;

FIG. 7 illustrates another example process flow that can facilitate determining loss of focus in online sessions, in accordance with an embodiment of this disclosure;

DETAILED DESCRIPTION

Overview

Bio telemetry data, such as electroencephalography (EEG) data, can be utilized to determine whether groups of learners have lost interest and focus during a virtual class. Virtual classrooms can bring with them an opportunity to perform training from any location, but can also bring with them a challenge of being able to understand the engagement level of the class. In general, in a physical classroom setting, there can be an ease to being able to naturally identify through body language and social cues when the instructor is losing the class's attention. The present techniques can be implemented to bridge a gap between the physical and the virtual by notifying an instructor when overall engagement levels are dropping across a class.

The present techniques can be implemented to leverage bots to present a web uniform resource locator (URL) in an online meeting chat that gives participants who have a bio telemetry device (e.g., a nearfield communication-enabled EEG headset) an ability to stream their bio telemetry data directly to the bot as part of information capture within a session. The bio telemetry data can be streamed to the bot and passed through a heuristic that makes a decision on whether or not the bot sends a notification to the instructor that the class is losing engagement.

Different brain waves in a student can represent different learning outcomes. It can be determined that, generally, during explicit learning tasks alpha brain waves (those with a frequency between 10 and 30 cycles per second) can increase in a student following the student correctly answering a question, and beta brain waves (those with a frequency between 3 and 7 cycles per second) can increase in a student following the student incorrectly answering a question. Alpha waves can increase in a student during explicit tasks, and decrease as the student progresses in learning.

Example Architectures

Figure 1:
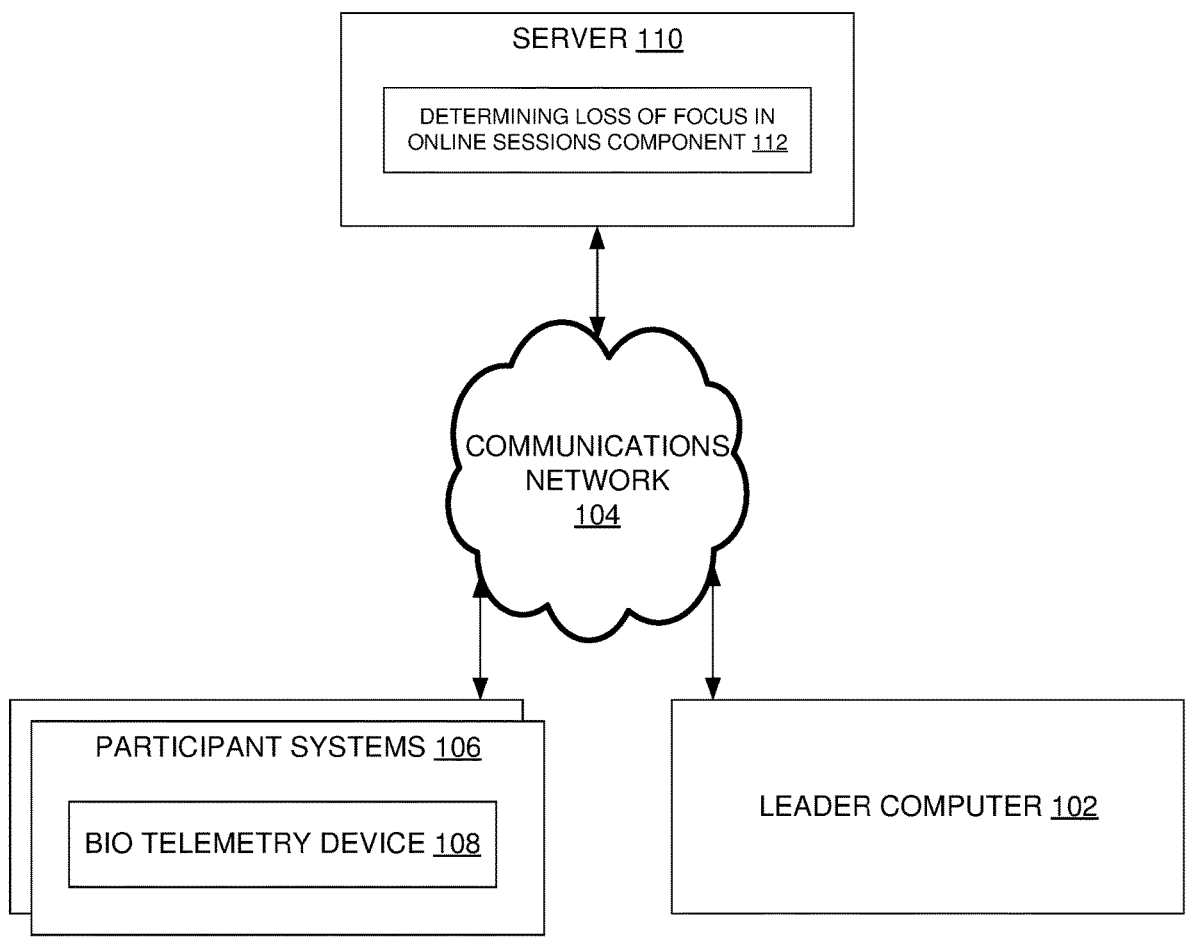
FIG. 1 illustrates an example system architecture that can facilitate determining loss of focus in online sessions, in accordance with an embodiment of this disclosure.

FIG. 1 illustrates an example system architecture 100 that can facilitate determining loss of focus in online sessions, in accordance with an embodiment of this disclosure.

System architecture 100 comprises leader computer 102, communications network 104, participant systems 106, and server 110. In turn, participant systems 106 comprise bio telemetry device 108, and server 110 comprises determining loss of focus in online sessions component 112.

Figure 8:
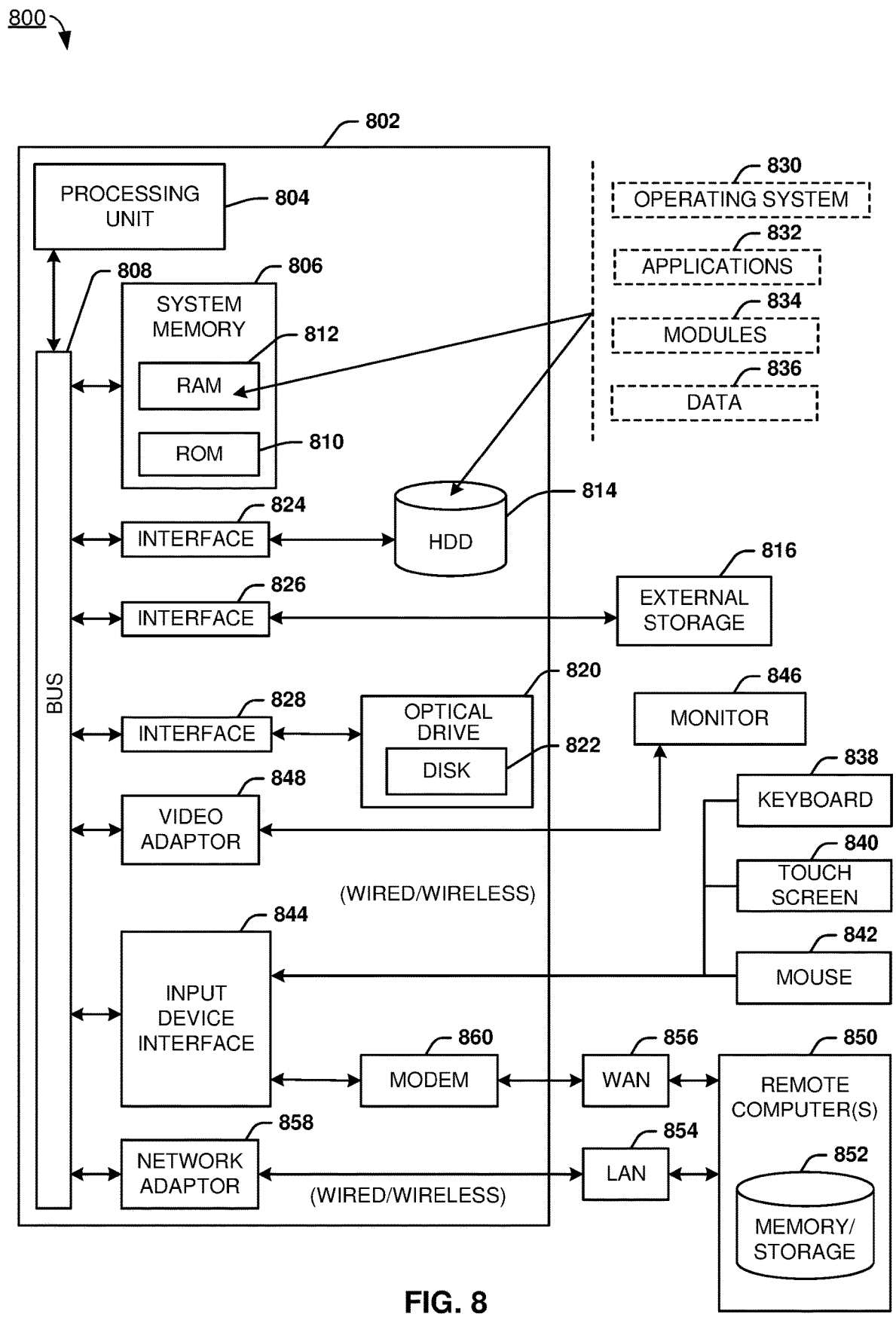
FIG. 8 illustrates an example block diagram of a computer operable to execute an embodiment of this disclosure.

Each of leader computer 102, participant systems 106, and server 110 can be implemented with part(s) of computing environment 800 of FIG. 8. Communications network 104 can comprise a computer communications network, such as the Internet.

In some examples, determining loss of focus in online sessions component 112 can implement part(s) of the process flows of FIGS. 3-7 to facilitate determining loss of focus in online sessions.

Multiple non-leader participants (e.g., students) in an online session can have an instance of participant systems 106. A participant system can comprise bio telemetry device 108 (e.g., an electroencephalography (EEG) device that measures a participants brain waves, or a heart rate monitor) and a corresponding computer. A participant can wear a bio telemetry device, which can measure time series information about the participant's body, such as a heart rate over time. This information can be transmitted from the participant's bio telemetry device to the participant's computer (e.g., via a near-field communication medium), and then to server 110.

Figure 3:
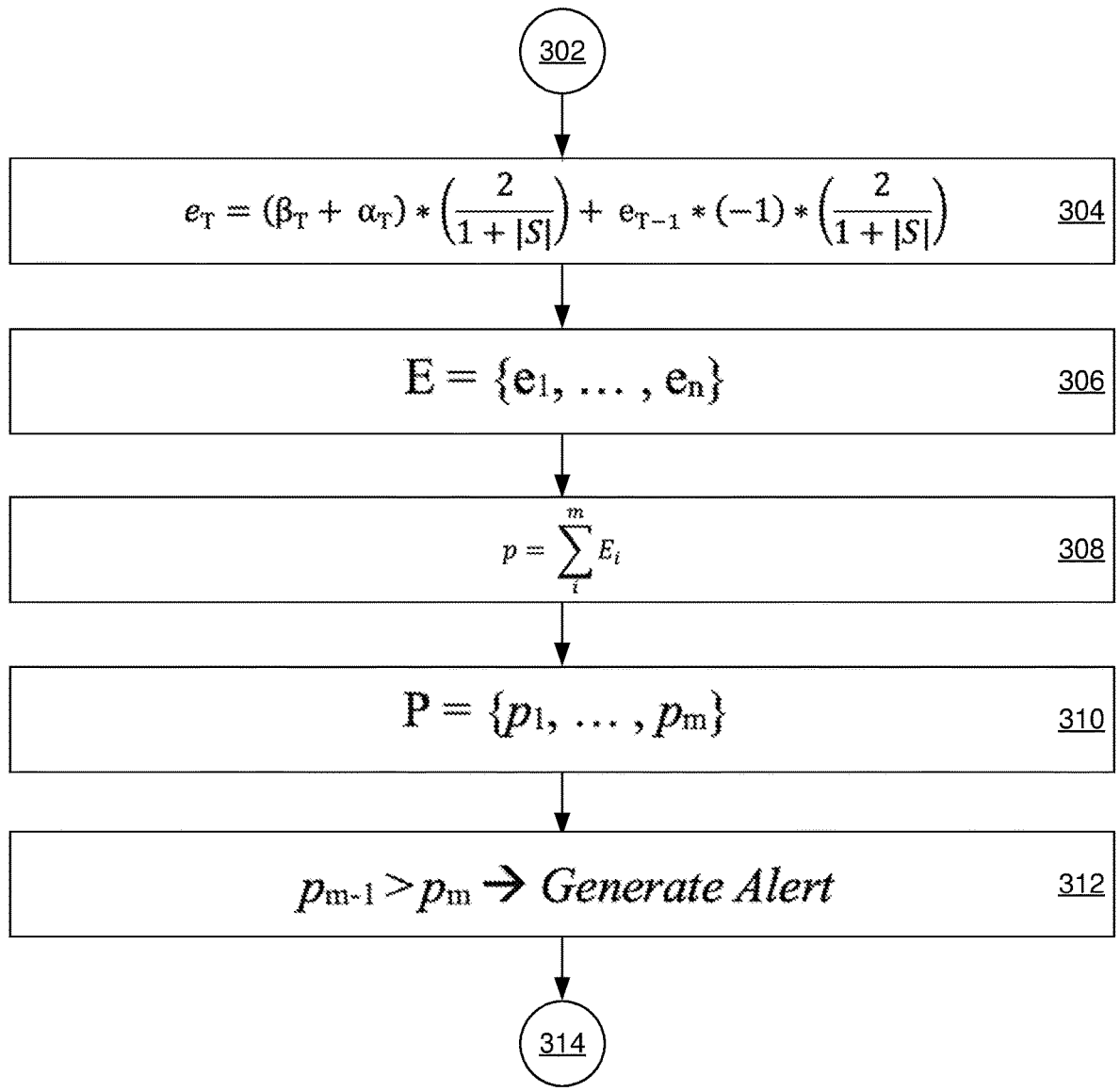
FIG. 3 illustrates an example process flow that can facilitate determining loss of focus in online sessions, in accordance with an embodiment of this disclosure.

Server 110 can receive and aggregate bio telemetry data from multiple participant systems, such as by determining loss of focus in online sessions component 112 implementing process flow 300 of FIG. 3. Where determining loss of focus in online sessions component 112 determines that there has been a loss of focus by online sessions participants, determining loss of focus in online sessions component 112 can send an alert indicating this loss of focus to leader computer 102.

It can be appreciated that system architecture 100 is one example system architecture for determining loss of focus in online sessions, and that there can be other system architectures (such as system architecture 200 of FIG. 2) that facilitate determining loss of focus in online sessions. For example, server 110 and leader computer 102 can be implemented on the same physical computer.

Figure 2:
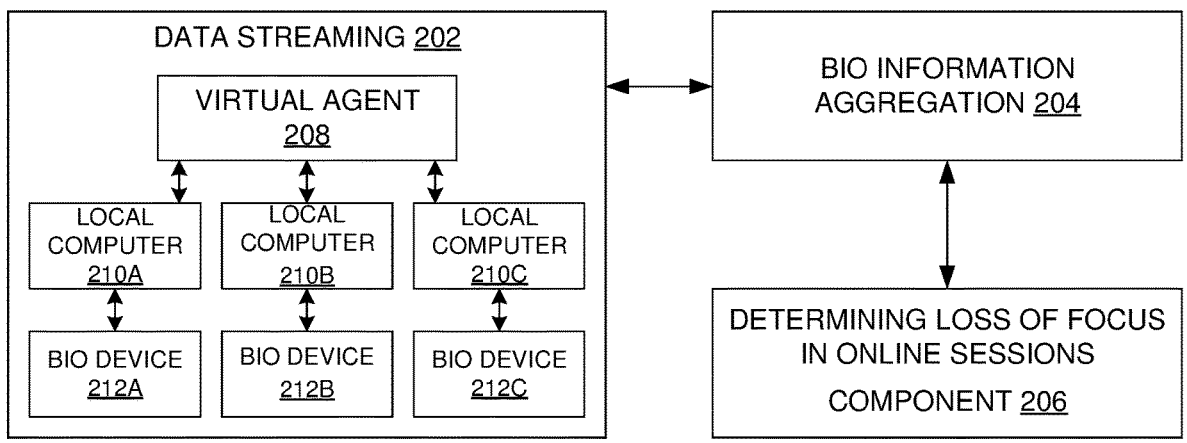
FIG. 2 illustrates another example system architecture that can facilitate determining loss of focus in online sessions, in accordance with an embodiment of this disclosure.

FIG. 2 illustrates another example system architecture 200 that can facilitate determining loss of focus in online sessions, in accordance with an embodiment of this disclosure. System architecture 200 can comprise an alternate system architecture, relative to system architecture 100 of FIG. 1, that can also facilitate determining loss of focus in online sessions.

System architecture 200 comprises data streaming 202, bio information aggregation 204, and facilitate determining loss of focus in online sessions component 206. In turn, data streaming 202 can comprise virtual agent 208, local computer 210A, local computer 210B, local computer 210C, bio device 212A, bio device 212B, and bio device 212C. While three local computers and three bio devices are depicted, it can be appreciated that the present techniques can be implemented with system architectures with more, or fewer, bio devices and computers.

Each of local computer 210A, local computer 210B, and local computer 210C can be similar to a computer of participant systems 106 of FIG. 1. Each of bio device 212A, bio device 212B, and bio device 212C can be similar to an instance of bio telemetry device 108 of FIG. 1.

Virtual agent 208 can communicate with each local computer to receive bio telemetry information that was originated by a bio device. Virtual agent 208 can also provide a login and/or consent user interface. For example, virtual agent 208 can comprise a web server that provides a web page to each local computer, where the web page allows a user to opt in to having their bio telemetry data shared, as well as to log in with credentials so that the user and their bio telemetry information can be associated with a user account.

Virtual agent 208 can forward bio telemetry data to bio information aggregation 204, which can comprise a computer component that aggregates bio telemetry information from multiple users. For example, bio information aggregation 204 can take an average of multiple users' bio telemetry data at a given point in time, and do this for each point in time for which there is data. In other examples, bio information aggregation 204 can sum multiple users' bio telemetry information for a given point in time, or otherwise numerically combine multiple users' bio telemetry information.

Once aggregated, bio information aggregation 204 can send the aggregated bio telemetry data to determining loss of focus in online sessions component 212, which can operate on the aggregated data in a similar manner as determining loss of focus in online sessions component 112 of FIG. 1.

Example Process Flows

FIG. 3 illustrates an example process flow that can facilitate determining loss of focus in online sessions, in accordance with an embodiment of this disclosure. In some examples, one or more embodiments of process flow 300 can be implemented by determining loss of focus in online sessions component 112 of FIG. 1, or computing environment 800 of FIG. 8.

It can be appreciated that the operating procedures of process flow 300 are example operating procedures, and that there can be embodiments that implement more or fewer operating procedures than are depicted, or that implement the depicted operating procedures in a different order than as depicted. In some examples, process flow 300 can be implemented in conjunction with one or more embodiments of one or more of process flow 400 of FIG. 4, process flow 500 of FIG. 5, process flow 600 of FIG. 6, and/or process flow 700 of FIG. 7.

Process flow 300 begins with 302, and moves to operation 304. Operation 304 depicts determining $e_T$ as follows:

$$e_T = (\beta_T + \alpha_T) * \left(\frac{2}{1+|S|}\right) + e_{T-1} * (-1) * \left(\frac{2}{1+|S|}\right)$$

where, $e_T$ =an exponential moving average at time T. T =time of current period, $\alpha$=alpha waves, $\beta$=beta waves, S={$T_1, \ldots, T_n$}, |S|=a number of elements in S.

This can produce an exponential moving average for a current time period. In some examples, the values for $\alpha$ and $\beta$ during a time period can vary over the time period. These values can be reduced to respective single values, such as by taking an average of the values over a time period. Where multiple users' data is used, data from multiple users can be combined into one value, such as by taking an average of the data of multiple users. In some examples, rather than averaging $\alpha$ and $\beta$ values over a time period, a single value at a point in time can be measured for each of $\alpha$ and $\beta$ for each time period, and that value can be used as the value for that time period.

In some examples, a number of time periods $T_1, \ldots, T_n$ is specified before the start of the online session. Sometimes online sessions can run longer and shorter than scheduled. It can be that the number of time periods does not line up with the actual length of the meeting, so long as the number of time periods is defined before the start of the meeting for determining an exponential moving average. For example, the number of time periods can be set at being far longer than the online session will likely run, or even can be set to be shorter than the session will likely run (where exponential moving averages continue to be determined for the session even though they exceed the number of time periods). In some examples, a length of a time period can be set to be a fraction of the anticipated length of the meeting, such as 2 minutes.

As time progresses, a set of these averages can be assembled in operation 306 as follows:

E={$e_1, \ldots, e_n$}

Here, the set E can comprise a collection of the moving averages that are determined in operation 306. From these averages, a sample of m exponential moving averages can be summed, which can be represented as p in operation 308:

$$p = \sum_i^m E_i$$

m can be selected to be a small number of exponential moving average values (e.g., 5 values). Then, these summed samples can be compared with each other to smooth out data (e.g., loss of focus is not detected when any two samples show a drop in attention over time, but when this loss of attention occurs over a longer time period).

In some examples, these samples p are non-overlapping. For example, $p_1$ can sum the first 5 values in E, $p_2$ can sum the next 5 values in E (e.g., values #6-10), etc.

These summed samples can be represented within a set, P, in operation 310:

P={$p_1, \ldots, p_m$}

A current p delta can be compared to a previous p delta. Where the current p delta is less than the previous p delta, that can indicate a drop in attentiveness across the class, as in operation 312:

$p_{m-1} > p_m \rightarrow$ Generate Alert

In some examples, an alert is generated when the drop in attentiveness is by at least a threshold amount, such as 10%. That is, operation 312 can be:

$p_{m-1} > 1.1 * p_m \rightarrow$ Generate Alert

This alert can be sent to a computer associated with a leader of the online session, such as an instructor.

FIG. 4 illustrates another example process flow 400 that can facilitate determining loss of focus in online sessions, in accordance with an embodiment of this disclosure. In some examples, one or more embodiments of process flow 400 can be implemented by determining loss of focus in online sessions component 112 of FIG. 1, or computing environment 800 of FIG. 8.

It can be appreciated that the operating procedures of process flow 400 are example operating procedures, and that there can be embodiments that implement more or fewer operating procedures than are depicted, or that implement the depicted operating procedures in a different order than as depicted. In some examples, process flow 400 can be implemented in conjunction with one or more embodiments of one or more of process flow 300 of FIG. 3, process flow 500 of FIG. 5, process flow 600 of FIG. 6, and/or process flow 700 of FIG. 7.

Process flow 400 begins with 402, and moves to operation 404. Operation 404 depicts receiving respective bio telemetry data from a group of people in an online session, wherein the bio telemetry data comprises alpha wave data and beta wave data, wherein the bio telemetry data spans a current time period. That is, bio telemetry data for multiple users can be determined, such as bio telemetry data generated by multiple instances of bio telemetry device 108 of FIG. 6.

In some examples, the alpha wave data corresponds to a first wave frequency of 8-12 cycles per second, and wherein the beta wave data corresponds to a second wave frequency of 12-35 cycles per second. That is, alpha waves and beta waves in a human brain can be distinguished from each other based on their frequency.

After operation 404, process flow 400 moves to operation 406.

Operation 406 depicts determining a current moving average for the current time period based on a numerical combination of respective beta wave data of the bio telemetry data and respective alpha wave data of the bio telemetry data, wherein the numerical combination is scaled by a first weighting value, wherein the current moving average is decreased by a previous moving average for a previous time period, and wherein the previous moving average is scaled by a second weighting value.

In some examples, the first weighting value is less than 1. In some examples, the second weighting value is less than 1. In some examples, the first weighting value equals the second weighting value. That is, in some examples, each of the first weighting value and the second weighting value can be (1/(2+|S|)).

After operation 406, process flow 400 moves to operation 408.

Operation 408 depicts, in response to determining that attentiveness by the group of people has decreased based on the previous moving average being greater than the current moving average, sending attentiveness notification data directed to a user account associated with an instructor of the online session. That is, it can be determined that attentiveness has decreased, so an alert can be sent to leader computer 102 of FIG. 1.

In some examples, the respective bio telemetry data is gathered by respective bio telemetry headsets of the respective people of the group of people, the respective bio telemetry headsets communicate with respective devices of the respective people, and the respective devices communicate with a central component that performs the determining of the current moving average and the sending of attentiveness notification data. That is, a system architecture similar to FIG. 1 can be implemented, where bio telemetry device 108 instances communicate with respective computers of participant systems 106, which then send the data to determining loss of focus in online sessions component 112 for processing.

In some examples, the respective bio telemetry headsets communicate with respective devices communicate via a first communications protocol, wherein the respective devices communicate with the central component via a second communications protocol, and wherein the first communications protocol differs from the second communications protocol. That is, the first communications protocol can comprise a Bluetooth communications protocol, and the second communications protocol can comprise a transmission control protocol/internet protocol (TCP/IP) protocol.

After operation 408, process flow 400 moves to 410, where process flow 400 ends.

FIG. 5 illustrates another example process flow 500 that can facilitate determining loss of focus in online sessions, in accordance with an embodiment of this disclosure. In some examples, one or more embodiments of process flow 500 can be implemented by determining loss of focus in online sessions component 112 of FIG. 1, or computing environment 800 of FIG. 8.

It can be appreciated that the operating procedures of process flow 500 are example operating procedures, and that there can be embodiments that implement more or fewer operating procedures than are depicted, or that implement the depicted operating procedures in a different order than as depicted. In some examples, process flow 500 can be implemented in conjunction with one or more embodiments of one or more of process flow 300 of FIG. 3, process flow 400 of FIG. 4, process flow 600 of FIG. 6, and/or process flow 700 of FIG. 7.

Process flow 500 begins with 502, and moves to operation 504. Operation 504 depicts receiving respective bio telemetry data from a group of people that are participants in an online meeting, wherein the bio telemetry data comprises alpha wave data and beta wave data, and wherein the bio telemetry data spans a current time period. In some examples, operation 504 can be implemented in a similar manner as operation 404 of FIG. 4.

In some examples, operation 404 comprises determining that respective people of the group of people have opted in to share respective portions of the bio telemetry data. In some examples, determining that the respective people have opted in is based on determining that the respective people have accessed respective uniform resource locators (URLs) indicative of opting in. That is, users can affirmatively opt in to sharing their bio telemetry data for a purpose of determining loss of focus in online sessions. One way that users can affirmatively opt in is by clicking on a web page link.

After operation 504, process flow 500 moves to operation 506.

Operation 506 depicts determining a current moving average for the current time period based on a numerical combination of respective beta wave data of the bio telemetry data and respective alpha wave data of the bio telemetry data, wherein the numerical combination is scaled by a first weighting value, wherein the current moving average is decreased by a previous moving average for a previous time period, and wherein the previous moving average is scaled by a second weighting value. In some examples, operation 506 can be implemented in a similar manner as operation 406 of FIG. 4.

In some examples, the first weighting value comprises a fraction, and wherein a denominator of the fraction comprises a number of time periods for which the bio telemetry data will be measured. That is, the first weighting value can be of the form $(1/|S|)$, such as with $(2/(1+|S|))$.

After operation 506, process flow 500 moves to operation 508.

Operation 508 depicts, in response to determining that the previous moving average is greater than the current moving average by at least a threshold amount, sending attentiveness notification data to a user account associated with the online meeting.

In some examples, operation 508 comprises determining the threshold amount as a function of the previous moving average that results in the threshold amount being a percentage of the previous moving average. That is, operation 310 (which depicts $p_{m-1} > p_m$ →Generate Alert), can involve requiring that $p_{m-1}$ be greater than $p_m$ by at least a percentage amount, such as an alert is generated where $p_{m-1}$ is at least 10% greater than $p_{m\ 1}$ (e.g., $p_{m-1} > 1.1 * p_m$ →Generate Alert).

After operation 508, process flow 500 moves to 510, where process flow 500 ends.

Figure 6:
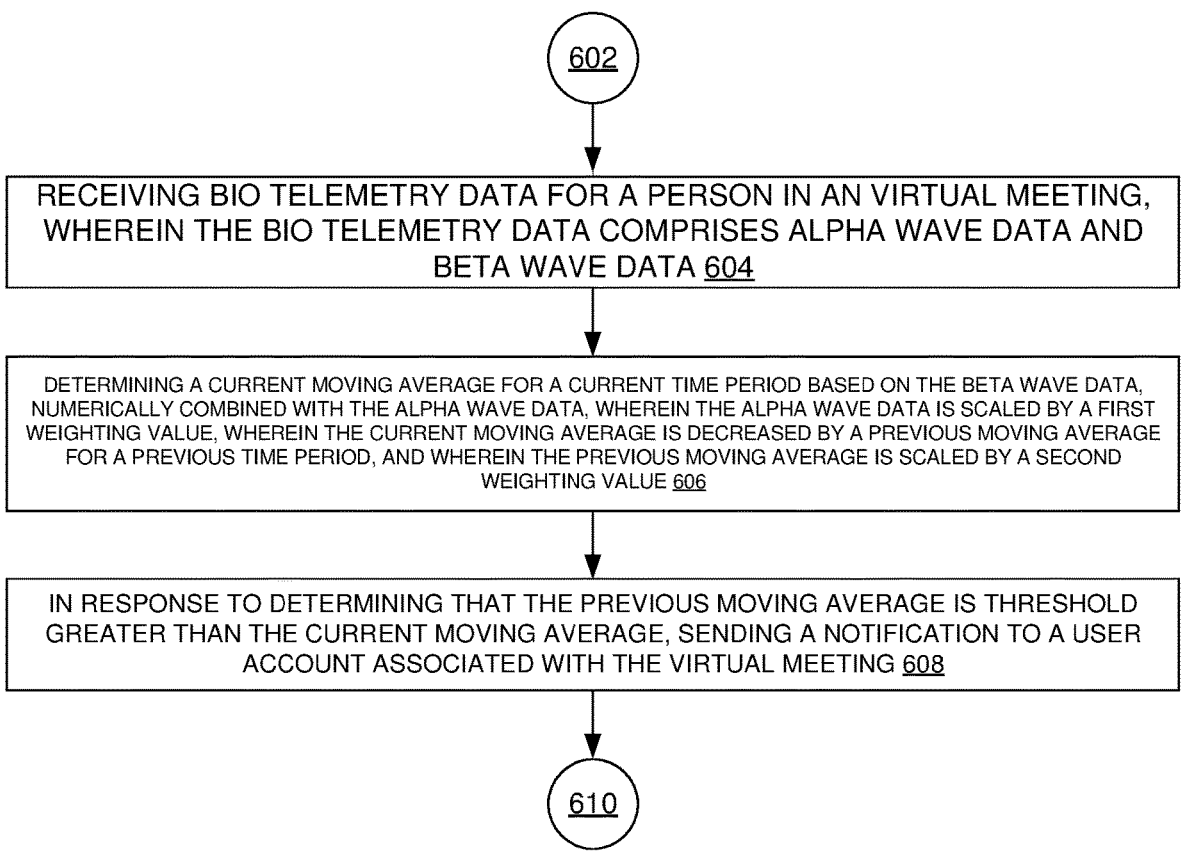
FIG. 6 illustrates another example process flow that can facilitate determining loss of focus in online sessions, in accordance with an embodiment of this disclosure.

FIG. 6 illustrates another example process flow 600 that can facilitate determining loss of focus in online sessions, in accordance with an embodiment of this disclosure. In some examples, one or more embodiments of process flow 600 can be implemented by determining loss of focus in online sessions component 112 of FIG. 1, or computing environment 800 of FIG. 8.

It can be appreciated that the operating procedures of process flow 600 are example operating procedures, and that there can be embodiments that implement more or fewer operating procedures than are depicted, or that implement the depicted operating procedures in a different order than as depicted. In some examples, process flow 600 can be implemented in conjunction with one or more embodiments of one or more of process flow 300 of FIG. 3, process flow 400 of FIG. 4, process flow 500 of FIG. 5, and/or process flow 700 of FIG. 7.

Process flow 600 begins with 602, and moves to operation 604. Operation 604 depicts receiving bio telemetry data for a person in an virtual meeting, wherein the bio telemetry data comprises alpha wave data and beta wave data. In some examples, operation 604 can be implemented in a similar manner as operation 404 of FIG. 4.

In some examples, operation 404 comprises determining that respective people of the group of people opt in to sharing respective bio telemetry data. In some examples, operation 404 comprises determining that the respective people opt in to sharing respective bio telemetry data based on determining that the respective people have accessed one or more uniform resource locators (URLs) indicative of opting in. That is, users can affirmatively opt in to sharing their bio telemetry data for a purpose of determining loss of focus in online sessions. One way that users can affirmatively opt in is by clicking on a web page link.

After operation 604, process flow 600 moves to operation 606.

Operation 606 depicts determining a current moving average for a current time period based on the beta wave data, numerically combined with the alpha wave data, wherein the alpha wave data is scaled by a first weighting value, wherein the current moving average is decreased by a previous moving average for a previous time period, and wherein the previous moving average is scaled by a second weighting value. In some examples, operation 606 can be implemented in a similar manner as operation 406 of FIG. 4.

In some examples, the first weighting value comprises a fraction, and a denominator of the fraction comprises a number of time periods for which the bio telemetry data has been measured. That is, the first weighting value can be of the form (1/|S|), such as with (2/(1+|S|)).

After operation 606, process flow 600 moves to operation 608.

Operation 608 depicts in response to determining that the previous moving average is threshold greater than the current moving average, sending a notification to a user account associated with the virtual meeting.

After operation 608, process flow 600 moves to 610, where process flow 600 ends.

FIG. 7 illustrates another example process flow 700 that can facilitate determining loss of focus in online sessions, in accordance with an embodiment of this disclosure. In some examples, one or more embodiments of process flow 700 can be implemented by determining loss of focus in online sessions component 112 of FIG. 1, or computing environment 800 of FIG. 8.

It can be appreciated that the operating procedures of process flow 700 are example operating procedures, and that there can be embodiments that implement more or fewer operating procedures than are depicted, or that implement the depicted operating procedures in a different order than as depicted. In some examples, process flow 700 can be implemented in conjunction with one or more embodiments of one or more of process flow 300 of FIG. 3, process flow 400 of FIG. 4, process flow 500 of FIG. 5, and/or process flow 600 of FIG. 6.

Process flow 700 begins with 702, and moves to operation 704. Operation 704 depicts creating multiple groups of moving averages, wherein the multiple groups of moving averages comprises the current moving average and the previous moving average, wherein respective groups of moving averages of the multiple groups of moving averages comprise a same number of moving averages. That is, using the example of FIG. 3, a set of moving averages, E, can be determined. From E, non-overlapping samples with n elements each can be generated to create summed samples p (e.g., in the set P={$p_1, \ldots, p_m$}. A group of moving average can be an element p.

In some examples, the current moving average and the previous moving average are each unique to one group of moving averages of the multiple groups of moving averages. That is, moving averages can be taken from non-overlapping windows, where one moving average is present in at most one window. For example, where there are twenty moving averages, arranged in an array [0-19], there can be four windows that span [0-4], [5-9], [10-14], and [15-19]. Using the above example of FIG. 3, group of moving averages can have n elements, where here n=5.

After operation 704, process flow 700 moves to operation 706.

Operation 706 depicts determining that the previous moving average is greater than the current moving average by at least the threshold amount based on determining that a first group of moving averages of the groups of moving averages is greater than a second group of moving averages of the groups of moving averages. That is, p values can be compared to generate an alert, such with $p_{m-1} > p_m \rightarrow$Generate Alert of FIG. 3.

After operation 706, process flow 700 moves to 708, where process flow 700 ends.

Example Operating Environment

In order to provide additional context for various embodiments described herein, FIG. 8 and the following discussion are intended to provide a brief, general description of a suitable computing environment 800 in which the various embodiments of the embodiment described herein can be implemented.

For example, parts of computing environment 800 can be used to implement one or more embodiments of leader computer 102, participant systems 106, and/or server 110 of FIG. 1, and/or data streaming 202, bio information aggregation 204, and/or determining loss of focus in online sessions component 206 of FIG. 2.

In some examples, computing environment 800 can implement one or more embodiments of the process flows of FIGS. 3-7 to facilitate determining loss of focus in online sessions.

While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the various methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 8, the example environment 800 for implementing various embodiments described herein includes a computer 802, the computer 802 including a processing unit 804, a system memory 806 and a system bus 808. The system bus 808 couples system components including, but not limited to, the system memory 806 to the processing unit 804. The processing unit 804 can be any of various commercially available processors. Dual microprocessors and other multi-processor architectures can also be employed as the processing unit 804.

The system bus 808 can be any of several types of bus structure that can further interconnect to a memory bus (with or without a memory controller), a peripheral bus, and a local bus using any of a variety of commercially available bus architectures. The system memory 806 includes ROM 810 and RAM 812. A basic input/output system (BIOS) can be stored in a nonvolatile storage such as ROM, erasable programmable read only memory (EPROM), EEPROM, which BIOS contains the basic routines that help to transfer information between elements within the computer 802, such as during startup. The RAM 812 can also include a high-speed RAM such as static RAM for caching data.

The computer 802 further includes an internal hard disk drive (HDD) 814 (e.g., EIDE, SATA), one or more external storage devices 816 (e.g., a magnetic floppy disk drive (FDD) 816, a memory stick or flash drive reader, a memory card reader, etc.) and an optical disk drive 820 (e.g., which can read or write from a CD-ROM disc, a DVD, a BD, etc.). While the internal HDD 814 is illustrated as located within the computer 802, the internal HDD 814 can also be configured for external use in a suitable chassis (not shown). Additionally, while not shown in environment 800, a solid state drive (SSD) could be used in addition to, or in place of, an HDD 814. The HDD 814, external storage device(s) 816 and optical disk drive 820 can be connected to the system bus 808 by an HDD interface 824, an external storage interface 826 and an optical drive interface 828, respectively. The interface 824 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 802, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 812, including an operating system 830, one or more application programs 832, other program modules 834 and program data 836. All or portions of the operating system, applications, modules, and/or data can also be cached in the RAM 812. The systems and methods described herein can be implemented utilizing various commercially available operating systems or combinations of operating systems.

Computer 802 can optionally comprise emulation technologies. For example, a hypervisor (not shown) or other intermediary can emulate a hardware environment for operating system 830, and the emulated hardware can optionally be different from the hardware illustrated in FIG. 8. In such an embodiment, operating system 830 can comprise one virtual machine (VM) of multiple VMs hosted at computer 802. Furthermore, operating system 830 can provide runtime environments, such as the Java runtime environment or the .NET framework, for applications 832. Runtime environments are consistent execution environments that allow applications 832 to run on any operating system that includes the runtime environment. Similarly, operating system 830 can support containers, and applications 832 can be in the form of containers, which are lightweight, standalone, executable packages of software that include, e.g., code, runtime, system tools, system libraries and settings for an application.

Further, computer 802 can be enable with a security module, such as a trusted processing module (TPM). For instance, with a TPM, boot components hash next in time boot components, and wait for a match of results to secured values, before loading a next boot component. This process can take place at any layer in the code execution stack of computer 802, e.g., applied at the application execution level or at the operating system (OS) kernel level, thereby enabling security at any level of code execution.

A user can enter commands and information into the computer 802 through one or more wired/wireless input devices, e.g., a keyboard 838, a touch screen 840, and a pointing device, such as a mouse 842. Other input devices (not shown) can include a microphone, an infrared (IR)

remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 804 through an input device interface 844 that can be coupled to the system bus 808, but can be connected by other interfaces, such as a parallel port, an IEEE 1394 serial port, a game port, a USB port, an IR interface, a BLUETOOTH® interface, etc.

A monitor 846 or other type of display device can be also connected to the system bus 808 via an interface, such as a video adapter 848. In addition to the monitor 846, a computer typically includes other peripheral output devices (not shown), such as speakers, printers, etc.

The computer 802 can operate in a networked environment using logical connections via wired and/or wireless communications to one or more remote computers, such as a remote computer(s) 850. The remote computer(s) 850 can be a workstation, a server computer, a router, a personal computer, portable computer, microprocessor-based entertainment appliance, a peer device or other common network node, and typically includes many or all of the elements described relative to the computer 802, although, for purposes of brevity, only a memory/storage device 852 is illustrated. The logical connections depicted include wired/wireless connectivity to a local area network (LAN) 854 and/or larger networks, e.g., a wide area network (WAN) 856. Such LAN and WAN networking environments are commonplace in offices and companies, and facilitate enterprise-wide computer networks, such as intranets, all of which can connect to a global communications network, e.g., the Internet.

When used in a LAN networking environment, the computer 802 can be connected to the local network 854 through a wired and/or wireless communication network interface or adapter 858. The adapter 858 can facilitate wired or wireless communication to the LAN 854, which can also include a wireless access point (AP) disposed thereon for communicating with the adapter 858 in a wireless mode.

When used in a WAN networking environment, the computer 802 can include a modem 860 or can be connected to a communications server on the WAN 856 via other means for establishing communications over the WAN 856, such as by way of the Internet. The modem 860, which can be internal or external and a wired or wireless device, can be connected to the system bus 808 via the input device interface 844. In a networked environment, program modules depicted relative to the computer 802 or portions thereof, can be stored in the remote memory/storage device 852. It will be appreciated that the network connections shown are example and other means of establishing a communications link between the computers can be used.

When used in either a LAN or WAN networking environment, the computer 802 can access cloud storage systems or other network-based storage systems in addition to, or in place of, external storage devices 816 as described above. Generally, a connection between the computer 802 and a cloud storage system can be established over a LAN 854 or WAN 856 e.g., by the adapter 858 or modem 860, respectively. Upon connecting the computer 802 to an associated cloud storage system, the external storage interface 826 can, with the aid of the adapter 858 and/or modem 860, manage storage provided by the cloud storage system as it would other types of external storage. For instance, the external storage interface 826 can be configured to provide access to cloud storage sources as if those sources were physically connected to the computer 802.

The computer 802 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Conclusion

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory in a single machine or multiple machines. Additionally, a processor can refer to an integrated circuit, a state machine, an application specific integrated circuit (ASIC), a digital signal processor (DSP), a programmable gate array (PGA) including a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units. One or more processors can be utilized in supporting a virtualized computing environment. The virtualized computing environment may support one or more virtual machines representing computers, servers, or other computing devices. In such virtualized virtual machines, components such as processors and storage devices may be virtualized or logically represented. For instance, when a processor executes instructions to perform "operations", this could include the processor performing the operations directly and/or facilitating, directing, or cooperating with another device or component to perform the operations.

In the subject specification, terms such as "datastore," "data storage," "database," "cache," and substantially any other information storage component relevant to operation and functionality of a component, refer to "memory components," or entities embodied in a "memory" or components comprising the memory. It will be appreciated that the memory components, or computer-readable storage media, described herein can be either volatile memory or nonvolatile storage, or can include both volatile and nonvolatile storage. By way of illustration, and not limitation, nonvolatile storage can include ROM, programmable ROM (PROM), EPROM, EEPROM, or flash memory. Volatile memory can include RAM, which acts as external cache memory. By way of illustration and not limitation, RAM can be available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

The illustrated embodiments of the disclosure can be practiced in distributed computing environments where certain tasks are performed by remote processing devices that are linked through a communications network. In a distributed computing environment, program modules can be located in both local and remote memory storage devices.

The systems and processes described above can be embodied within hardware, such as a single integrated circuit (IC) chip, multiple ICs, an ASIC, or the like. Further, the order in which some or all of the process blocks appear in each process should not be deemed limiting. Rather, it should be understood that some of the process blocks can be executed in a variety of orders that are not all of which may be explicitly illustrated herein.

As used in this application, the terms "component," "module," "system," "interface," "cluster," "server," "node," or the like are generally intended to refer to a computer-related entity, either hardware, a combination of hardware and software, software, or software in execution or an entity related to an operational machine with one or more specific functionalities. For example, a component can be, but is not limited to being, a process running on a processor, a processor, an object, an executable, a thread of execution, computer-executable instruction(s), a program, and/or a computer. By way of illustration, both an application running on a controller and the controller can be a component. One or more components may reside within a process and/or thread of execution and a component may be localized on one computer and/or distributed between two or more computers. As another example, an interface can include input/output (I/O) components as well as associated processor, application, and/or application programming interface (API) components.

Further, the various embodiments can be implemented as a method, apparatus, or article of manufacture using standard programming and/or engineering techniques to produce software, firmware, hardware, or any combination thereof to control a computer to implement one or more embodiments of the disclosed subject matter. An article of manufacture can encompass a computer program accessible from any computer-readable device or computer-readable storage/communications media. For example, computer readable storage media can include but are not limited to magnetic storage devices (e.g., hard disk, floppy disk, magnetic strips...), optical discs (e.g., CD, DVD...), smart cards, and flash memory devices (e.g., card, stick, key drive...). Of course, those skilled in the art will recognize many modifications can be made to this configuration without departing from the scope or spirit of the various embodiments.

In addition, the word "example" or "exemplary" is used herein to mean serving as an example, instance, or illustration. Any embodiment or design described herein as "exemplary" is not necessarily to be construed as preferred or advantageous over other embodiments or designs. Rather, use of the word exemplary is intended to present concepts in a concrete fashion. As used in this application, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What has been described above includes examples of the present specification. It is, of course, not possible to describe every conceivable combination of components or methods for purposes of describing the present specification, but one of ordinary skill in the art may recognize that many further combinations and permutations of the present specification are possible. Accordingly, the present specification is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system, comprising:
    a processor; and
    a memory that stores executable instructions that, when executed by the processor, facilitate performance of operations, comprising:
        receiving respective bio telemetry data from a group of people in an online session, wherein the bio telemetry data comprises alpha wave data and beta wave data, wherein the bio telemetry data spans a current time period;
        determining a current moving average for the current time period based on a numerical combination of respective beta wave data of the bio telemetry data and respective alpha wave data of the bio telemetry data, wherein the numerical combination is scaled by a first weighting value, wherein the current moving average is decreased by a previous moving average for a previous time period, and wherein the previous moving average is scaled by a second weighting value; and
        in response to determining that attentiveness by the group of people has decreased based on the previous moving average being greater than the current moving average, sending attentiveness notification data directed to a user account associated with an instructor of the online session.

2. The system of claim 1, wherein the respective bio telemetry data is gathered by respective bio telemetry headsets of the respective people of the group of people, wherein the respective bio telemetry headsets communicate with respective devices of the respective people, and wherein the respective devices communicate with a central component that performs the determining of the current moving average and the sending of attentiveness notification data.

3. The system of claim 2, wherein the respective bio telemetry headsets communicate with respective devices communicate via a first communications protocol, wherein the respective devices communicate with the central component via a second communications protocol, and wherein the first communications protocol differs from the second communications protocol.

4. The system of claim 1, wherein the alpha wave data corresponds to a first wave frequency of 8-12 cycles per second, and wherein the beta wave data corresponds to a second wave frequency of 12-35 cycles per second.

5. The system of claim 1, wherein the first weighting value is less than 1.

6. The system of claim 1, wherein the second weighting value is less than 1.

7. The system of claim 1, wherein the first weighting value equals the second weighting value.

8. A method, comprising:
receiving, by a system comprising a processor, respective bio telemetry data from a group of people that are participants in an online meeting, wherein the bio telemetry data comprises alpha wave data and beta wave data, and wherein the bio telemetry data spans a current time period;
determining, by the system, a current moving average for the current time period based on a numerical combination of respective beta wave data of the bio telemetry data and respective alpha wave data of the bio telemetry data, wherein the numerical combination is scaled by a first weighting value, wherein the current moving average is decreased by a previous moving average for a previous time period, and wherein the previous moving average is scaled by a second weighting value; and
in response to determining that the previous moving average is greater than the current moving average by at least a threshold amount, sending, by the system, attentiveness notification data to a user account associated with the online meeting.

9. The method of claim 8, wherein the first weighting value comprises a fraction, and wherein a denominator of the fraction comprises a number of time periods for which the bio telemetry data will be measured.

10. The method of claim 8, further comprising:
creating, by the system, multiple groups of moving averages, wherein the multiple groups of moving averages comprises the current moving average and the previous moving average, wherein respective groups of moving averages of the multiple groups of moving averages comprise a same number of moving averages; and
wherein the determining that the previous moving average is greater than the current moving average by at least the threshold amount comprises determining, by the system, that a first group of moving averages of the groups of moving averages is greater than a second group of moving averages of the groups of moving averages.

11. The method of claim 10, wherein the current moving average and the previous moving average are each unique to one group of moving averages of the multiple groups of moving averages.

12. The method of claim 8, further comprising:
determining, by the system, that respective people of the group of people have opted in to share respective portions of the bio telemetry data.

13. The method of claim 12, wherein the determining that the respective people have opted in is based on determining that the respective people have accessed respective uniform resource locators (URLs) indicative of opting in.

14. The method of claim 8, further comprising:
determining, by the system, the threshold amount as a function of the previous moving average that results in the threshold amount being a percentage of the previous moving average.

15. A non-transitory computer-readable medium comprising instructions that, in response to execution, cause a system comprising a processor to perform operations, comprising:
receiving bio telemetry data for a person in an virtual meeting, wherein the bio telemetry data comprises alpha wave data and beta wave data;
determining a current moving average for a current time period based on the beta wave data, numerically combined with the alpha wave data, wherein the alpha wave data is scaled by a first weighting value, wherein the current moving average is decreased by a previous moving average for a previous time period, and wherein the previous moving average is scaled by a second weighting value; and
in response to determining that the previous moving average is threshold greater than the current moving average, sending a notification to a user account associated with the virtual meeting.

16. The non-transitory computer-readable medium of claim 15, wherein the bio telemetry data comprises electroencephalography (EEG) data.

17. The non-transitory computer-readable medium of claim 15, wherein the first weighting value comprises a fraction, and wherein a denominator of the fraction comprises a number of time periods for which the bio telemetry data has been measured.

18. The non-transitory computer-readable medium of claim 15, wherein the operations further comprise:
creating multiple groups of moving averages, wherein the multiple groups of moving averages comprises the current moving average and the previous moving average, wherein respective groups of moving averages of the multiple groups of moving averages comprise a same number of moving averages; and
wherein the determining that the previous moving average is greater than the current moving average by at least the threshold amount comprises determining that a first group of moving averages of the groups of moving averages is greater than a second group of moving averages of the groups of moving averages.

19. The non-transitory computer-readable medium of claim 18, wherein the current moving average and the previous moving average are each unique to one group of moving averages of the multiple groups of moving averages.

20. The non-transitory computer-readable medium of claim 15, wherein the operations further comprise:
determining that respective people of the group of people opt in to sharing respective bio telemetry data.

* * * * *